(12) United States Patent
Palmer et al.

(10) Patent No.: US 7,809,437 B2
(45) Date of Patent: Oct. 5, 2010

(54) METHODS AND SYSTEMS FOR REMOVING ACCUMULATED CHARGE FROM ONE OR MORE ELECTRODES

(75) Inventors: Logan P. Palmer, Santa Monica, CA (US); Lakshmi N. Mishra, Valencia, CA (US); Mike A. Faltys, Northridge, CA (US)

(73) Assignee: Advanced Bionics, LLC, Valencia, CA (US)

( * ) Notice: Subject to any disclaimer, the term of this patent is extended or adjusted under 35 U.S.C. 154(b) by 346 days.

(21) Appl. No.: 11/599,004

(22) Filed: Nov. 13, 2006

(65) Prior Publication Data

US 2008/0114405 A1     May 15, 2008

(51) Int. Cl.
*A61N 1/18*     (2006.01)
(52) U.S. Cl. .................................. 607/2; 607/5; 607/63
(58) Field of Classification Search ..................... 607/5, 607/7, 56–57, 63, 2
See application file for complete search history.

(56) References Cited

U.S. PATENT DOCUMENTS

| | | | |
|---|---|---|---|
| 4,202,341 A * | 5/1980 | Blaser ............................ 607/9 |
| 4,408,608 A | 10/1983 | Daly et al. |
| 4,592,359 A | 6/1986 | Galbraith |
| 4,819,647 A | 4/1989 | Byers et al. |
| 4,947,844 A | 8/1990 | McDermott |
| 5,193,539 A | 3/1993 | Schulman et al. |
| 5,193,540 A | 3/1993 | Schulman et al. |
| 5,312,439 A | 5/1994 | Loeb |
| 5,501,703 A | 3/1996 | Holsheimer et al. |
| 5,522,865 A | 6/1996 | Schulman et al. |
| 5,531,774 A | 7/1996 | Schulman et al. |
| 5,574,633 A | 11/1996 | Prater |
| 5,674,264 A | 10/1997 | Carter et al. |
| 5,938,688 A | 8/1999 | Schiff |
| 6,016,449 A | 1/2000 | Fischell et al. |
| 6,035,237 A * | 3/2000 | Schulman et al. ............. 607/63 |
| 6,051,017 A | 4/2000 | Loeb et al. |
| 6,129,753 A | 10/2000 | Kuzma |
| 6,164,284 A | 12/2000 | Schulman et al. |
| 6,185,452 B1 | 2/2001 | Schulman et al. |
| 6,208,894 B1 | 3/2001 | Schulman et al. |
| 6,301,505 B1 * | 10/2001 | Money ........................ 607/63 |
| 6,487,446 B1 | 11/2002 | Hill et al. |
| 6,516,227 B1 | 2/2003 | Meadows et al. |
| 6,539,263 B1 | 3/2003 | Schiff et al. |
| 2001/0052986 A1 * | 12/2001 | Nantel et al. ................. 356/625 |
| 2005/0015133 A1 | 1/2005 | Ibrahim et al. |
| 2005/0101878 A1 | 5/2005 | Daly et al. |
| 2006/0004424 A1 * | 1/2006 | Loeb et al. ..................... 607/63 |
| 2008/0015641 A1 * | 1/2008 | Armstrong et al. ............. 607/2 |

* cited by examiner

*Primary Examiner*—Carl H Layno
*Assistant Examiner*—Pamela M Bays
(74) *Attorney, Agent, or Firm*—AdvantEdge Law Group, LLC

(57) ABSTRACT

Methods of removing accumulated charge from one or more electrodes include applying a plurality of stimulation events to one or more stimulation sites within a patient via the one or more electrodes and globally shorting each of the electrodes during a plurality of global shorting periods interspersed among the plurality of stimulation events. Systems for removing accumulated charge from one or more electrodes include a stimulator electrically coupled to the one or more electrodes and configured to apply a plurality of stimulation events to one or more stimulation sites within a patient via the one or more electrodes. The stimulator is further configured to globally short each of the electrodes during a plurality of global shorting periods interspersed among the plurality of stimulation events.

15 Claims, 9 Drawing Sheets

METHODS AND SYSTEMS FOR REMOVING ACCUMULATED CHARGE FROM ONE OR MORE ELECTRODES

BACKGROUND

Radio-frequency (RF) powered implantable stimulators and battery powered implantable stimulators are described in the art. See, for instance, U.S. Pat. No. 5,193,539 ("Implantable Microstimulator"); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. Nos. 6,164,284 and 6,208,894 (both entitled "System of Implantable Device for Monitoring and/or Affecting Body Parameters"). Each of these patents is incorporated herein by reference in its respective entirety.

A wide variety of medical conditions and disorders have been successfully treated using implantable stimulators. For example, implantable stimulators have been used to treat hearing disorders, urinary urge incontinence, headaches, and various other muscular and neural disorders.

To illustrate, the sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The electrical stimulation pulses may then be applied directly to auditory nerves within the cochlea via one or more of the electrodes.

The electrical stimulation pulses generated by implantable stimulators are often biphasic. A biphasic electrical stimulation pulse includes two parts—a negative first phase and a positive second phase. It is often desirous for a biphasic stimulation pulse to be charge-balanced. In other words, it is desirous for the stimulation pulse to include an equal amount of negative charge and positive charge. However, because of inherent imperfections in current sources that generate the negative and positive phases of a stimulation pulse, charge imbalances often occur wherein an unequal amount of positive and negative charge is applied via one or more electrodes.

Over time, charge imbalances may result in excess charge accumulating on the electrodes that are coupled to an implantable stimulator. Eventually, the built-up charge may inhibit stimulation and/or cause device malfunction.

Various approaches have been taken to eliminate charge build-up or accumulation on the electrodes of implantable stimulators. In some systems, DC-blocking capacitors are placed in series with the electrodes in order to block or eliminate long term DC current. However, DC-blocking capacitors require significant printed circuit board (PCB) space. Moreover, the charge build-up will still occur, albeit on the DC-blocking capacitors rather than on the electrodes. As a result, a DC bias voltage across the capacitors may form, which, if sufficiently large, may inhibit stimulation.

Bleed resistors have also been used to eliminate charge build-up. Bleed resistors remove built-up charge on the electrodes by dissipating the charge as heat. However, bleed resistors are relatively large and therefore undesirable in many implantable stimulators. Additionally, bleed resistors effectively reduce the accuracy of the current sources that generate the stimulation pulses because they shunt some of the stimulation current away from the electrodes.

SUMMARY

Methods of removing accumulated charge from one or more electrodes include applying a plurality of stimulation events to one or more stimulation sites within a patient via the one or more electrodes and globally shorting each of the electrodes during a plurality of global shorting periods interspersed among the plurality of stimulation events.

Systems for removing accumulated charge from one or more electrodes include a stimulator electrically coupled to the one or more electrodes and configured to apply a plurality of stimulation events to one or more stimulation sites within a patient via the one or more electrodes. The stimulator is further configured to globally short each of the electrodes during a plurality of global shorting periods interspersed among the plurality of stimulation events.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for removing accumulated charge from one or more electrodes coupled to a stimulator or any other device are described herein. In some examples, a stimulator may be configured to apply a plurality of stimulation events to one or more stimulation sites within a patient via the one or more electrodes. Each stimulation event may include one or more biphasic stimulation pulses, for example. The stimulator may be further configured to globally short each of the electrodes during a plurality of global shorting periods interspersed among the plurality of stimulation events. In this manner, excess charge that has accumulated on the electrodes may be removed therefrom.

The methods and systems described herein may be used to maintain charge balance in stimulation systems, prevent charge build-up on electrodes, and optimize the overall stimulation experience for a patient. However, it will be recognized that the methods and systems described herein may be used for any additional or alternative purpose as best serves a particular application.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
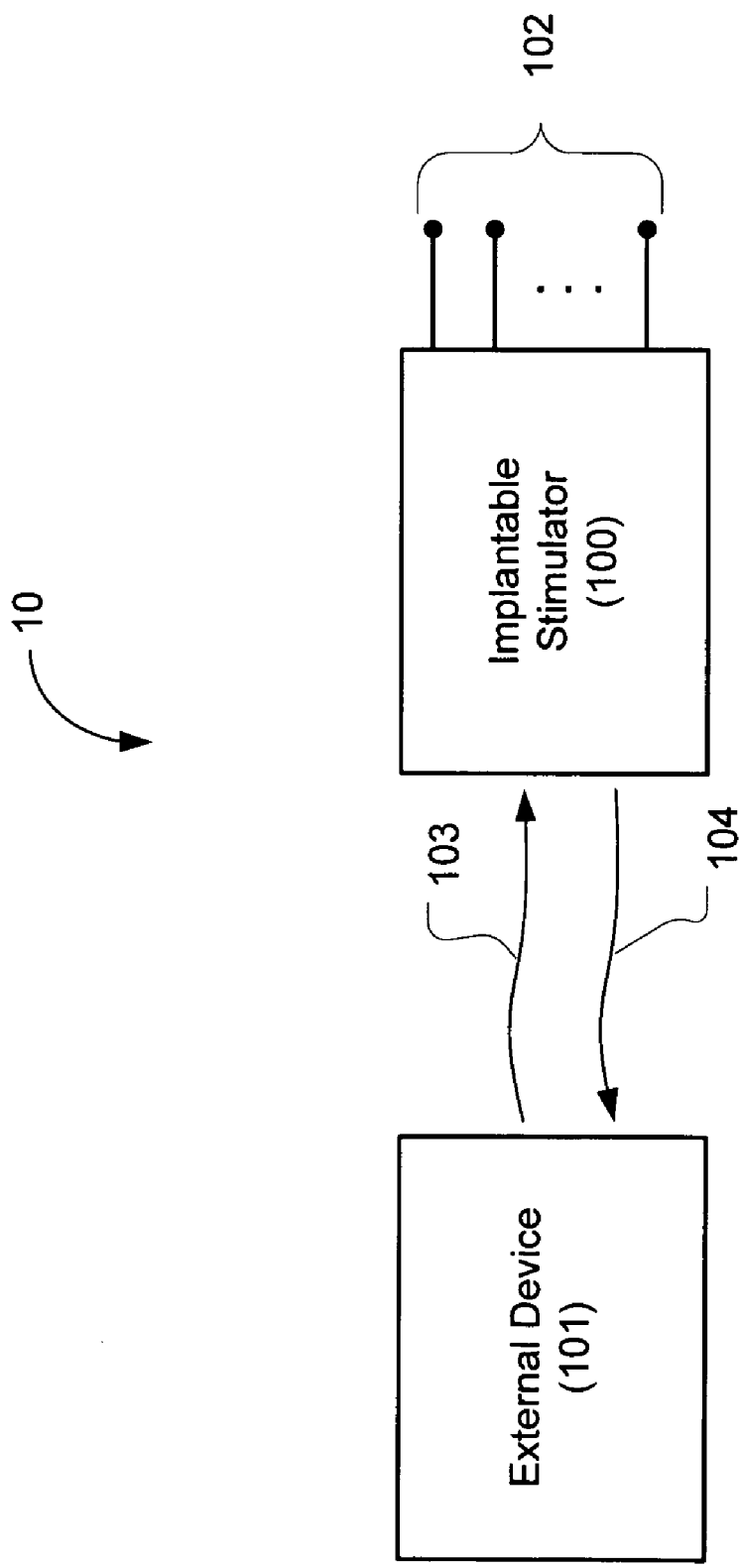
FIG. 1 illustrates an exemplary stimulation system according to principles described herein.

FIG. 1 illustrates an exemplary stimulation system (10). As shown in FIG. 1, the system (10) includes an implantable stimulator (100) configured to communicate with an external device (101) via one or more communication links (103, 104). It will be recognized that the stimulator (100) of FIG. 1 is merely illustrative of the many different types of implantable devices that may be used in connection with the systems and methods described herein.

As shown in FIG. 1, the implantable stimulator (100) may include a number of electrodes (102) that may be configured to apply an electrical stimulation current to one or more stimulation sites within a patient. The function of the electrodes (102) will be described in more detail below.

The external device (101) may include any device configured to communicate with and/or control the implantable stimulator (100). For example, the external device (101) may include, but is not limited to, a signal processor or any other type of speech processor, a programming device, and/or an external power charger. In some examples, the external device (101) may be configured to transmit control data, stimulation parameters, power signals, and/or other signals to the stimulator (100) via a first communication link (103), also referred to as a forward-telemetry link. Likewise, the implantable stimulator (100) may be configured to transmit status signals and/or other signals to the external device (101) via a second communication link (104), also referred to as a back-telemetry link. In some alternative examples, the first and second communication links (103, 104) may be combined into a single bidirectional communication link.

Figure 2:
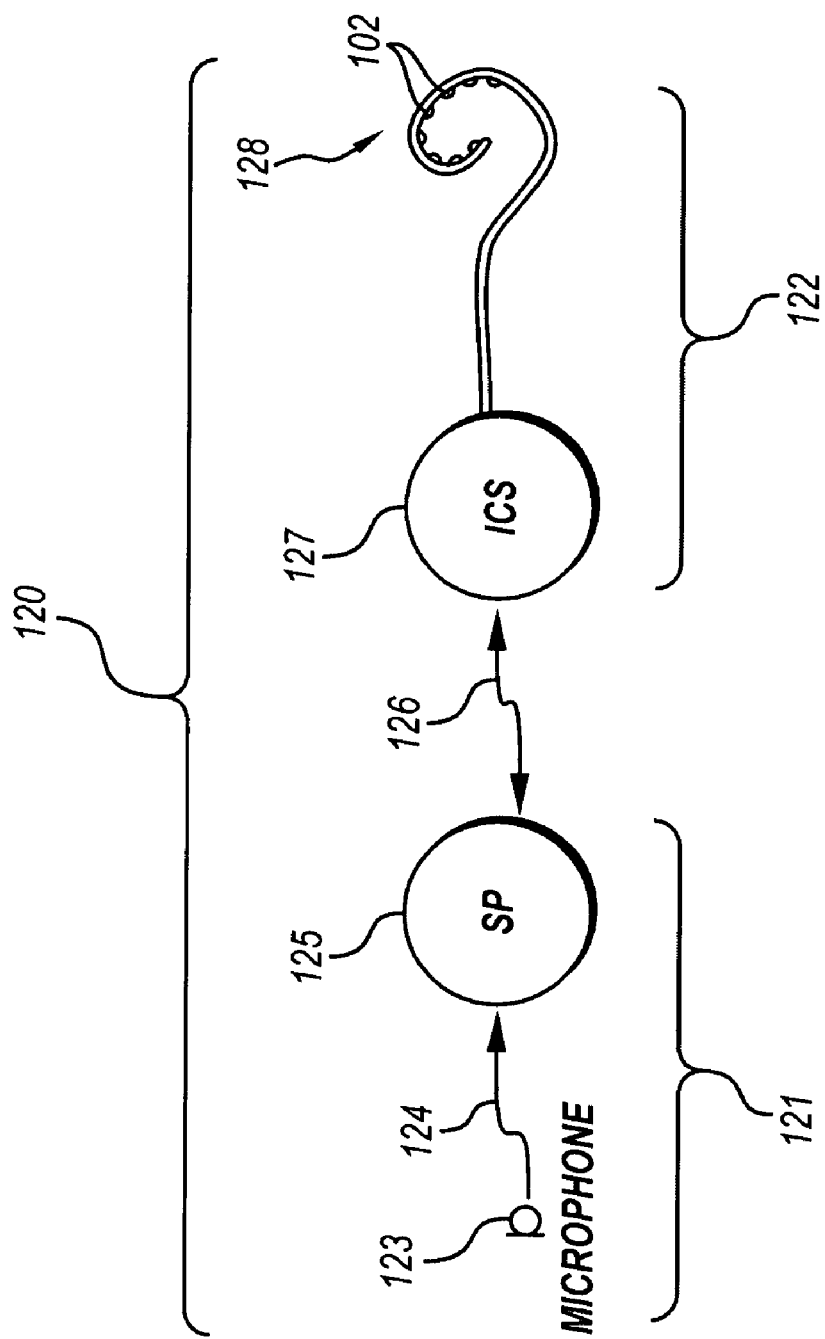
FIG. 2 illustrates an exemplary cochlear implant system according to principles described herein.

A number of exemplary implantable stimulators with which the present systems and methods may be employed will now be described. FIG. 2 illustrates an exemplary cochlear implant system (120) that may be used as an implantable stimulator in accordance with the present systems and methods. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties.

The cochlear implant system (120) of FIG. 2 includes a signal processor portion (121) and a cochlear stimulation portion (122). The signal processor portion (121) may include a microphone (123), a signal processor (SP) (125), and/or additional circuitry as best serves a particular application. The cochlear stimulation portion (122) may include an implantable cochlear stimulator (ICS) (127), a number of electrodes (102) disposed on a lead (128), and/or additional circuitry as best serves a particular application. The components within the signal processor portion (121) and the cochlear stimulation portion (122) will be described in more detail below.

The microphone (123) of FIG. 2 is configured to sense acoustic signals and convert the sensed signals to corresponding electrical signals. The electrical signals are sent from the microphone (123) to the SP (125) via a communication link (124). Alternatively, the microphone (123) may be connected directly to, or integrated with, the SP (125). The SP (125) processes these converted acoustic signals in accordance with a selected signal processing strategy to generate appropriate stimulation parameters for controlling the ICS (127). These parameters may specify or define the polarity, magnitude, location (i.e., which electrode pair or electrode group receive the stimulation current), and timing (i.e., when the stimulation current is to be applied to a particular electrode pair) of the electrical stimulation pulses that are generated by the ICS (127).

The lead (128) of FIG. 2 is configured to be inserted within a duct of the cochlea. As shown in FIG. 2, the lead (128) includes a multiplicity of electrodes (102), e.g., sixteen electrodes, spaced along its length. It will be understood, however, that any number of electrodes (102) may be disposed on the lead (128). The lead (128) may be substantially as shown and described in U.S. Pat. No. 4,819,647 or U.S. Pat. No. 6,129,753, each of which is incorporated herein by reference in its respective entirety. Electronic circuitry within the ICS (127) is configured to generate stimulation current via selected pairs or groups of the individual electrodes (102) in accordance with a specified stimulation pattern defined by the SP (125).

The ICS (127) and the SP (125) may be electronically connected via a suitable data or communication link (126). It will be understood that the data communication link (126) may include a bi-directional communication link and/or one or more dedicated uni-directional communication links, such as the forward and back-telemetry links (103, 104) shown in FIG. 1.

In some examples, the SP (125) and the microphone (123) comprise an external portion of the cochlear implant system (120) and the ICS (127) and the electrode lead (128) comprise an implantable portion of the system (120) that is implanted within a patient's body. In alternative embodiments, one or more portions of the SP (125) are included within the implantable portion of the cochlear implant system (120).

The external and implantable portions of the cochlear implant system (120) may each include one or more coils configured to transmit and receive power and/or control signals via the communication link (126). For example, the external portion of the cochlear implant system (120) may include an external coil (not shown) and the implantable portion of the cochlear implant system (120) may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of the cochlear implant system (120). It will be noted that, in some embodiments, both the SP (125) and the ICS (127) may be implanted within the patient, either in the same housing or in separate housings. If the SP (125) and the ICS (127) are in the same housing, the communication link (126) may be realized with a direct wire connection within such housing. If the SP (125) and the ICS (127) are in separate housings, the communication link (126) may include one or more inductive links, for example.

Figures 3A, 3B:
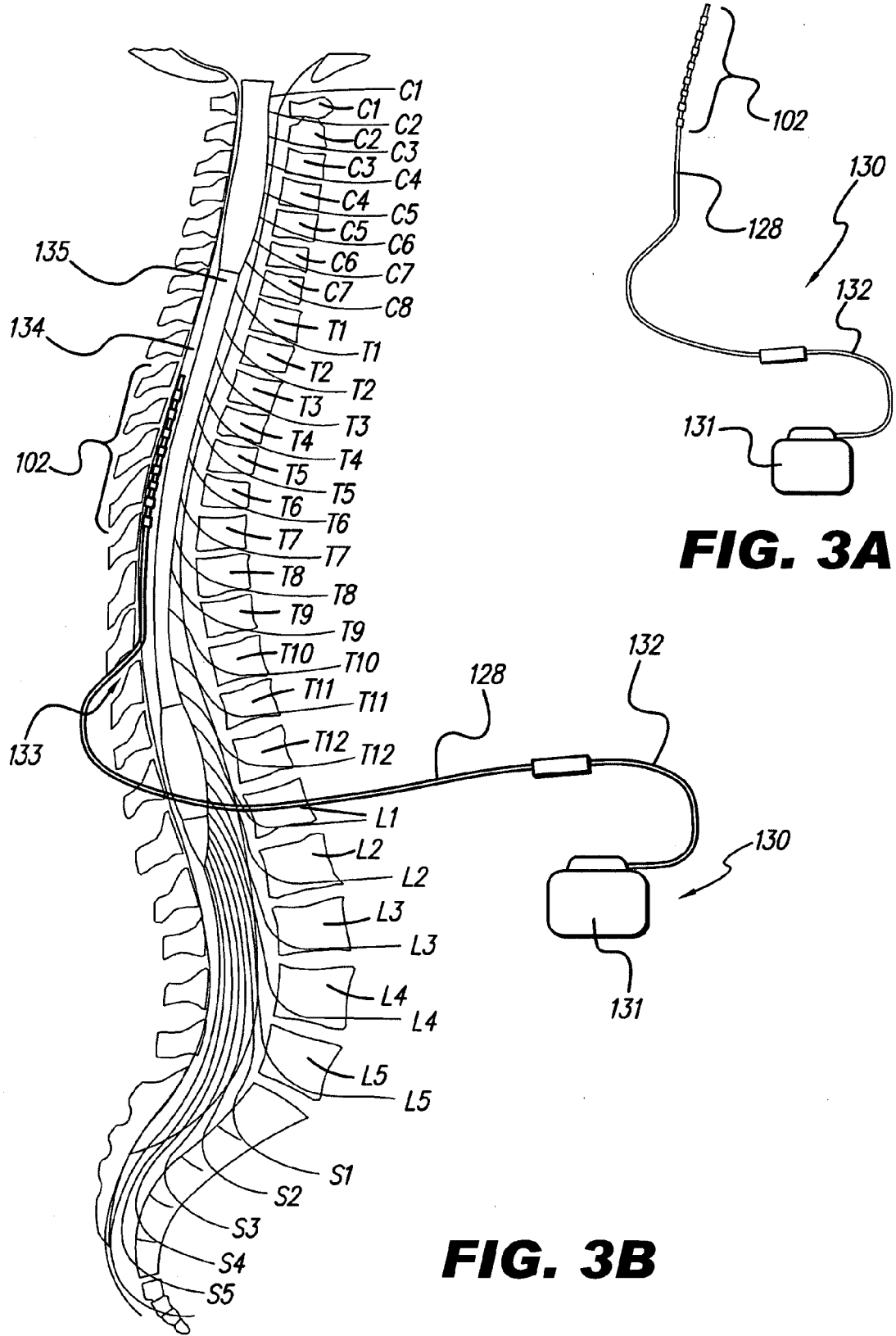
FIGS. 3A and 3B illustrate an exemplary spinal cord stimulator system according to principles described herein.

The implantable stimulator (100) of FIG. 1 may alternatively include a spinal cord stimulator (SCS). FIGS. 3A and 3B illustrate an exemplary spinal cord stimulator system (130). The SCS (130) may be used to treat a number of different medical conditions such as, but not limited to, chronic pain.

As shown in FIG. 3A, the SCS (130) may include an implantable pulse generator (IPG) (131), a lead extension (132), and a lead (128) having an array of electrodes (102) disposed thereon. The electrodes (102) may be arranged, as shown in FIG. 3A, in an in-line array near the distal end of the lead (128). Other electrode array configurations may additionally or alternatively be used. For example, the electrodes (102) may be arranged on a paddle lead. It will be recognized that the lead extension (132) is optional and that it may be used as desired depending on the physical distance between the IPG (131) and the stimulation site within the patient. The IPG (131) is configured to generate electrical stimulation pulses that are applied to a stimulation site via one or more of the electrodes (102). Exemplary spinal cord stimulators suitable for use as described herein include, but are not limited to, those disclosed in U.S. Pat. Nos. 5,501,703; 6,487,446; and 6,516,227, all of which are incorporated herein by reference in their respective entireties.

FIG. 3B shows that the array of electrodes (102) of the SCS (130) may be implanted in the epidural space (134) of a patient in close proximity to the spinal cord (135). Because of the lack of space near the lead exit point (133) where the electrode lead (128) exits the spinal column, the IPG (131) is generally implanted in the abdomen or above the buttocks. However, it will be recognized that the IPG (131) may be implanted at any suitable implantation site within a patient.

The cochlear implant system (120; FIG. 2) and the SCS (130; FIG. 3A) are merely illustrative of many types of stimulators that may be implanted within a patient and configured to apply one or more stimuli at a stimulation site. For example, the implantable stimulator (100) may additionally or alternatively include a deep brain stimulator, an implantable microstimulator, or any other type of stimulator configured to perform neural response imaging. Exemplary deep brain stimulators suitable for use as described herein include, but are not limited to, those disclosed in U.S. Pat. Nos. 5,938,688; 6,016,449; and 6,539,263. Exemplary implantable microstimulators, such as the BION® microstimulator (Advanced Bionics® Corporation, Valencia, Calif.), suitable for use as described herein include, but are not limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 4:
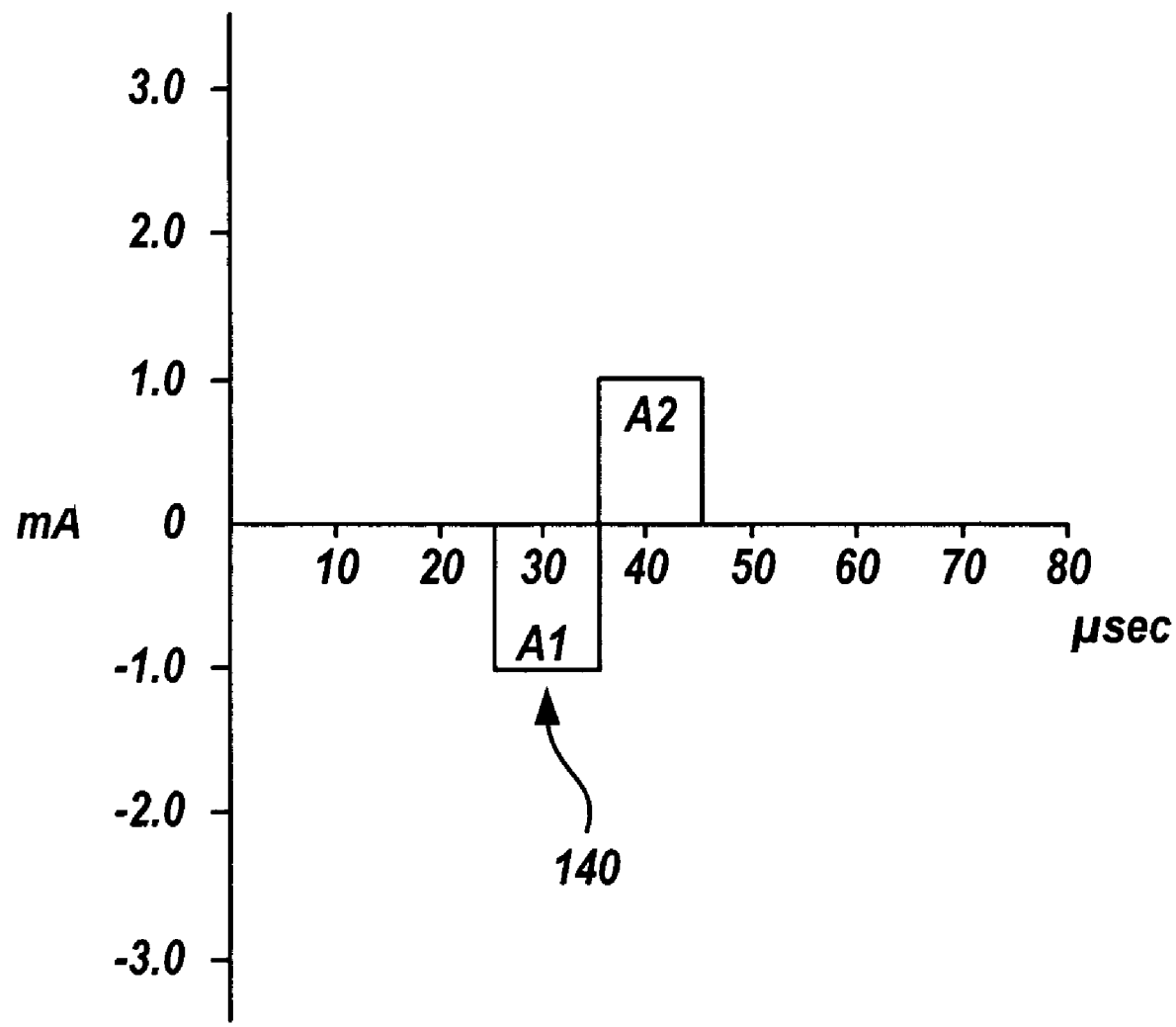
FIG. 4 illustrates an electrical stimulation pulse that may be delivered to one or more stimulation sites within a patient via one or more of the electrodes according to principles described herein.

FIG. 4 illustrates an electrical stimulation pulse (140) that may be delivered to one or more stimulation sites within a patient via one or more of the electrodes (102). The stimulation pulse (140) of FIG. 4 is biphasic. In other words, the stimulation pulse (140) includes two parts—a negative first phase having an area A1 and a positive second phase having an area A2. In some implementations, the negative phase A1 causes neural tissue to depolarize or fire. The stimulation pulse (140) shown in FIG. 4 has an amplitude of 1 milliamp (mA) and a pulse width of 20 microseconds (μsec) for illustrative purposes only. It will be recognized that any of the characteristics of the stimulation pulse (140), including, but not limited to, the pulse shape, amplitude, pulse width, frequency, burst pattern (e.g., burst on time and burst off time), duty cycle or burst repeat interval, ramp on time, and ramp off time may vary as best serves a particular application. Moreover, it will be recognized that other types of stimulation current may be delivered to one or more stimulation sites in accordance with the methods and systems described herein including, but not limited to, alterphasic pulses, alternating DC current, etc.

As mentioned, it is often desirable for the stimulation pulse (140) to be charge-balanced. The stimulation pulse (140) of FIG. 4 is illustrative of a charged-balanced stimulation pulse because its negative area A1 is equal to its positive area A2. Charge-balanced stimulation pulses (130) are often used to minimize the accumulation of charge at the electrodes (102), which can cause electrode corrosion and harm to surrounding tissue.

However, because of inherent imperfections in current sources that generate the negative and positive phases of a stimulation pulse, charge imbalances often occur wherein an unequal amount of positive and negative charge is applied via one or more electrodes. As mentioned, charge imbalances may result in excess charge accumulation or build-up on the electrodes, which may inhibit stimulation and/or cause device malfunction. Hence, as will be described in more detail below, the stimulator (100) may be configured to at least intermittently short one or more electrodes (102) in order to remove accumulated charge therefrom. As will be described in more detail below, a particular electrode (102) may be shorted by connecting the electrode (102) to ground or to a reference electrode for a specified amount of time.

Figure 5:
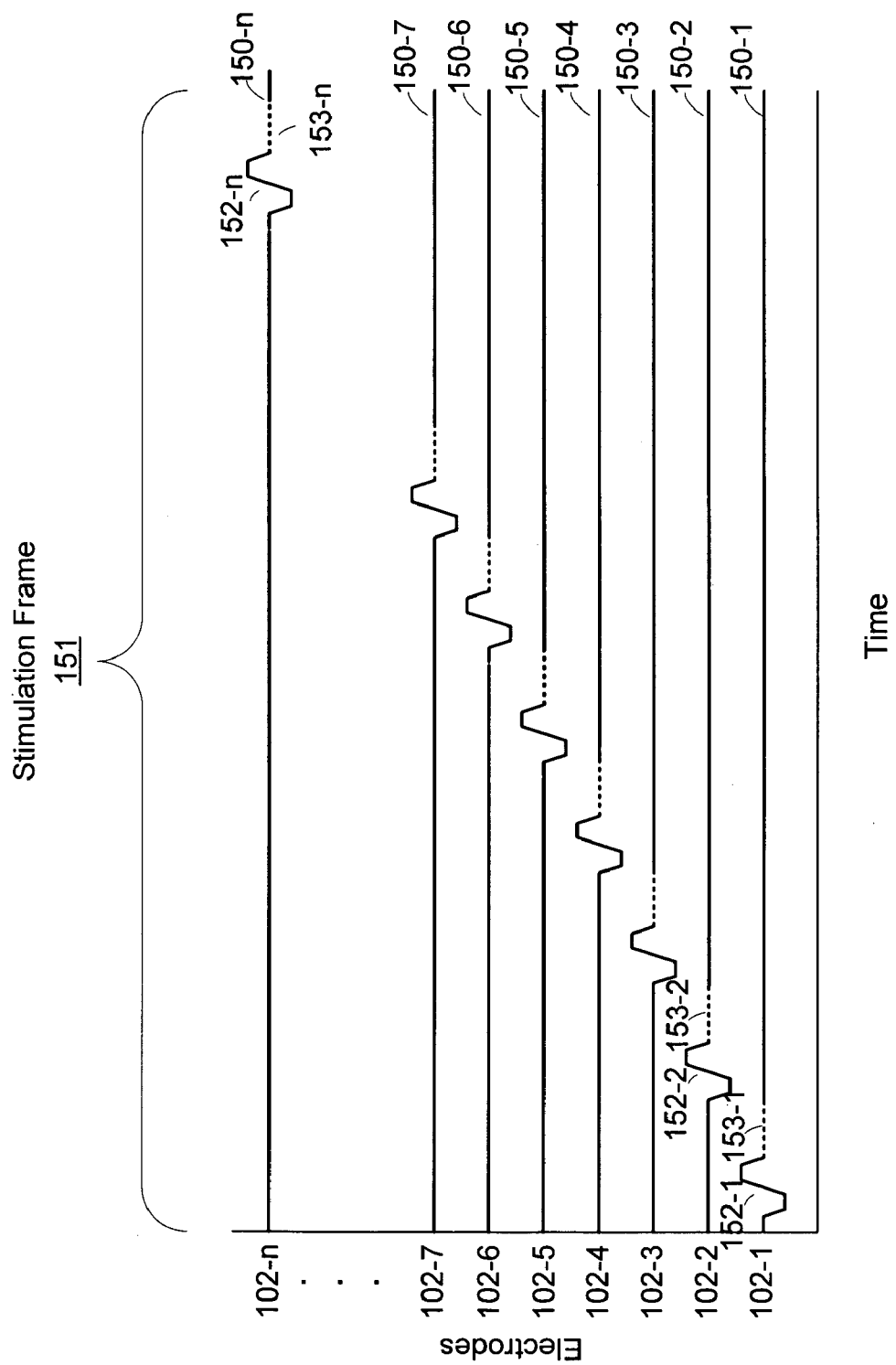
FIG. 5 is a waveform diagram illustrating an exemplary method of shorting one or more electrodes in order to remove accumulated charge therefrom according to principles described herein.

FIG. 5 is a waveform diagram illustrating an exemplary method of shorting one or more electrodes (102) in order to remove accumulated charge therefrom. The diagram of FIG. 5 shows a number of exemplary stimulation pulse waveforms (150-1 through 150-n) that may be applied to one or more stimulation sites via each electrode (102-1 through 102-n) during a particular stimulation frame (151). Each waveform (150) shown in FIG. 5 includes a stimulation event (152) that may include one or more stimulation pulses, for example. However, for illustrative purposes only, each stimulation event (152) shown in FIG. 5 includes a single biphasic stimulation pulse.

As shown in FIG. 5, each stimulation event (152) is immediately followed by a time period (153) referred to herein as a "shorting period." Each shorting period is indicated in FIG. 5 by a horizontal dashed line. For example, the stimulation event labeled 152-1 that is applied via the electrode labeled 102-1 is immediately followed by the shorting period labeled 153-1. It will be recognized that the duration of each of the stimulation events (152) and shorting periods (153) may vary as best serves a particular application.

During each shorting period (153) of FIG. 5, a corresponding electrode (102) is shorted. As will be described in more detail below, the electrode (102) may be shorted by connecting the electrode (102) to ground, a reference electrode, or any other reference voltage. By shorting the electrode (102) for a sufficient length of time, excess charge that has accumulated on the electrode (102) is removed.

However, because each shorting period (153) immediately follows a corresponding stimulation event (152), charge from the stimulation event (152) is effectively removed from the vicinity of the corresponding electrode (102) almost immediately after the charge is applied. Hence, the shorting method of FIG. 5 often leads to a reduction in the efficiency of the stimulation event (152) in terms of energy applied to the neurons that are stimulated.

Moreover, the duration of each shorting period (153) in FIG. 5 has to be long enough to allow all of the accumulated charge to be removed from the electrodes (102). As used herein, the term "full shorting period" will be used to refer to the amount of time required to fully remove accumulated charge from an electrode (102). However, stimulation cannot be applied via any of the electrodes (102) while a particular electrode is being shorted. For example, as shown in FIG. 5, the stimulation event labeled 152-2 cannot be applied until after the shorting period labeled 153-1 is completed. Hence, if the full shorting period (153) of each electrode (102) is relatively long and if a full shorting period (153) follows each stimulation event (152), as shown in FIG. 5, the amount of actual stimulation applied via the electrodes (102) in any given time period (i.e., the overall stimulation rate of the stimulator (100)) is sub-optimal.

Hence, in some examples, a global shorting scheme wherein all of the electrodes (102) are at least intermittently shorted at the same time may be used to remove accumulated charge therefrom. As will be described in more detail below, the global shorting scheme may be configured to optimize the stimulation efficiency and the overall stimulation rate of the stimulator (100).

Figure 6:
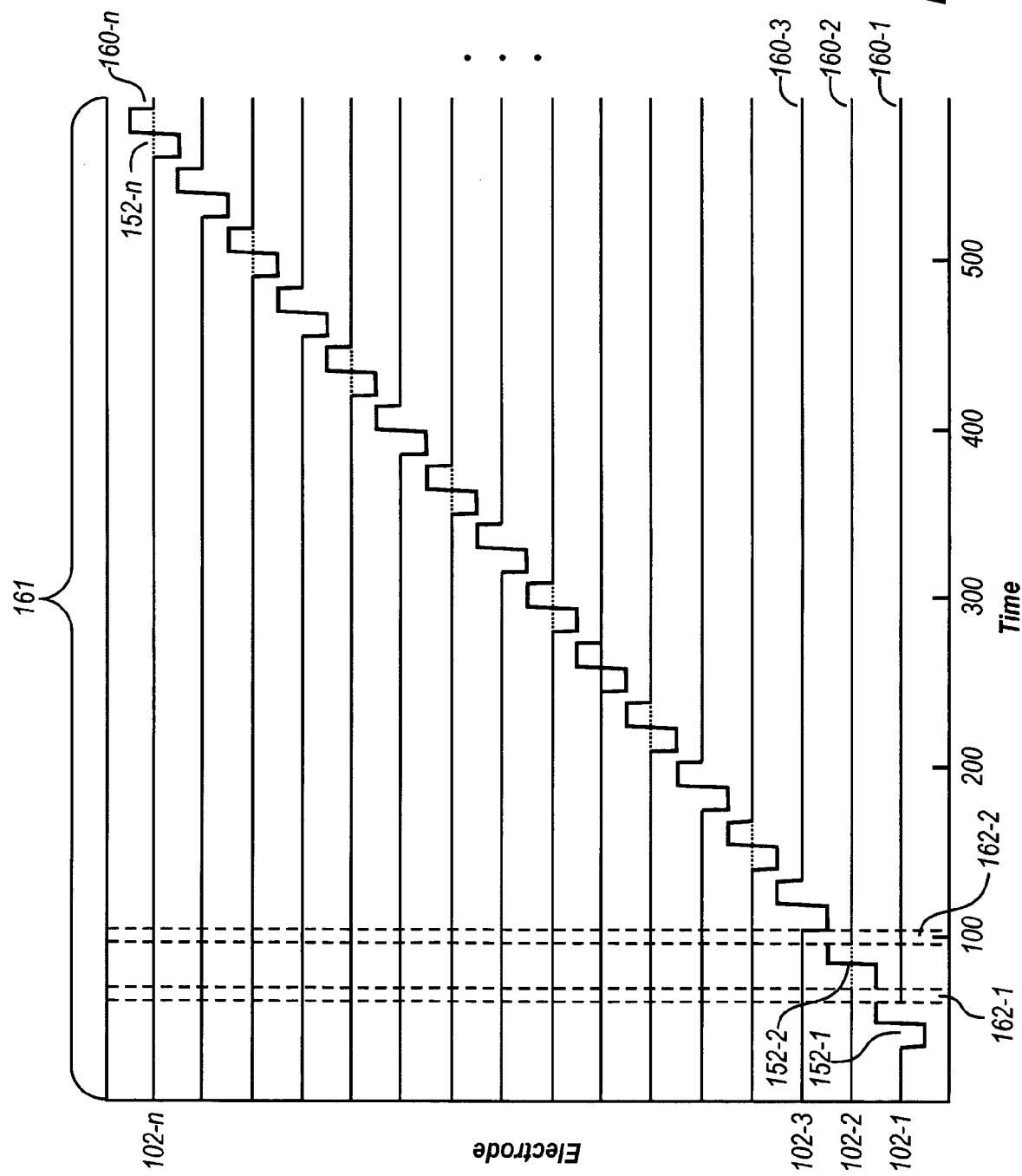
FIG. 6 illustrates an exemplary global shorting scheme wherein all of the electrodes are periodically shorted at the same time in order to remove accumulated charge therefrom according to principles described herein.

FIG. 6 illustrates an exemplary global shorting scheme wherein all of the electrodes (102) are periodically shorted at the same time in order to remove accumulated charge therefrom. The diagram of FIG. 6 shows a number of exemplary stimulation pulse waveforms (160-1 through 160-n) that may be applied to one or more stimulation sites via each electrode (102-1 through 102-n) during a particular stimulation frame (161). Each waveform (160) shown in FIG. 6 includes a stimulation event (152) that may include one or more stimulation pulses, for example. However, for illustrative purposes only, each stimulation event (152) shown in FIG. 6 includes a single biphasic stimulation pulse.

As shown in FIG. 6, a number of global shorting periods (162) are interspersed among the stimulation events (152). For example, as shown in FIG. 6, each stimulation event (152) may be immediately followed by a global shorting period (162). To illustrate, the beginning and end times of the first two global shorting periods (162-1 and 162-2) are indicated by vertical dashed lines.

During each global shorting period (162), all of the electrodes (102) are globally shorted. As used herein, the term "global short" and variations thereof will be used to mean simultaneously shorting at least a group of the electrodes (102) or shorting at least a group of electrodes (102) within a pre-defined time period. As will be described in more detail below, the electrodes (102) may be shorted by connecting each of the electrodes (102) to ground, a reference electrode, or any other reference voltage.

Because each electrode (102) is shorted after each stimulation event (152), at least a portion of the accumulated charge on each electrode (102) is removed after each stimulation event (152) is applied. Hence, the accumulated charge on each electrode (102) is removed over time in a distributed fashion.

To illustrate, as shown in FIG. 6, a first stimulation event (152-1) may be applied via the first electrode (102-1) during a first time period. Immediately after the first stimulation event (152-1), all of the electrodes (102) are globally shorted during a first global shorting period (162-1). During the first global shorting period (162-1), a portion of the charge that accumulated on the first electrode (102-1) during the first stimulation event (152-1) is removed therefrom. The process is repeated as subsequent stimulation events (152) and global shorting periods (162) occur during the stimulation frame (161). With each subsequent global shorting period (162-1), additional portions of the charge that accumulated on the first electrode (102-1) during the first stimulation event (152-1) are removed therefrom until all of accumulated charge has been removed.

Because only a portion of accumulated charge is removed from each electrode (102) during each global shorting period (162), each global shorting period (162) may have a shorter duration than the full shorting periods (153) of FIG. 5. Hence, with relatively short duration global shorting periods (162), the efficiency of the stimulation events (152) may be optimized by avoiding immediate removal of all charge from the vicinity of each of the electrodes (102). Moreover, the relatively short duration global shorting periods (162) allow more stimulation to be applied to one or more stimulation sites during a given time period, thus optimizing the overall stimulation rate of the stimulator (100).

Figure 7:
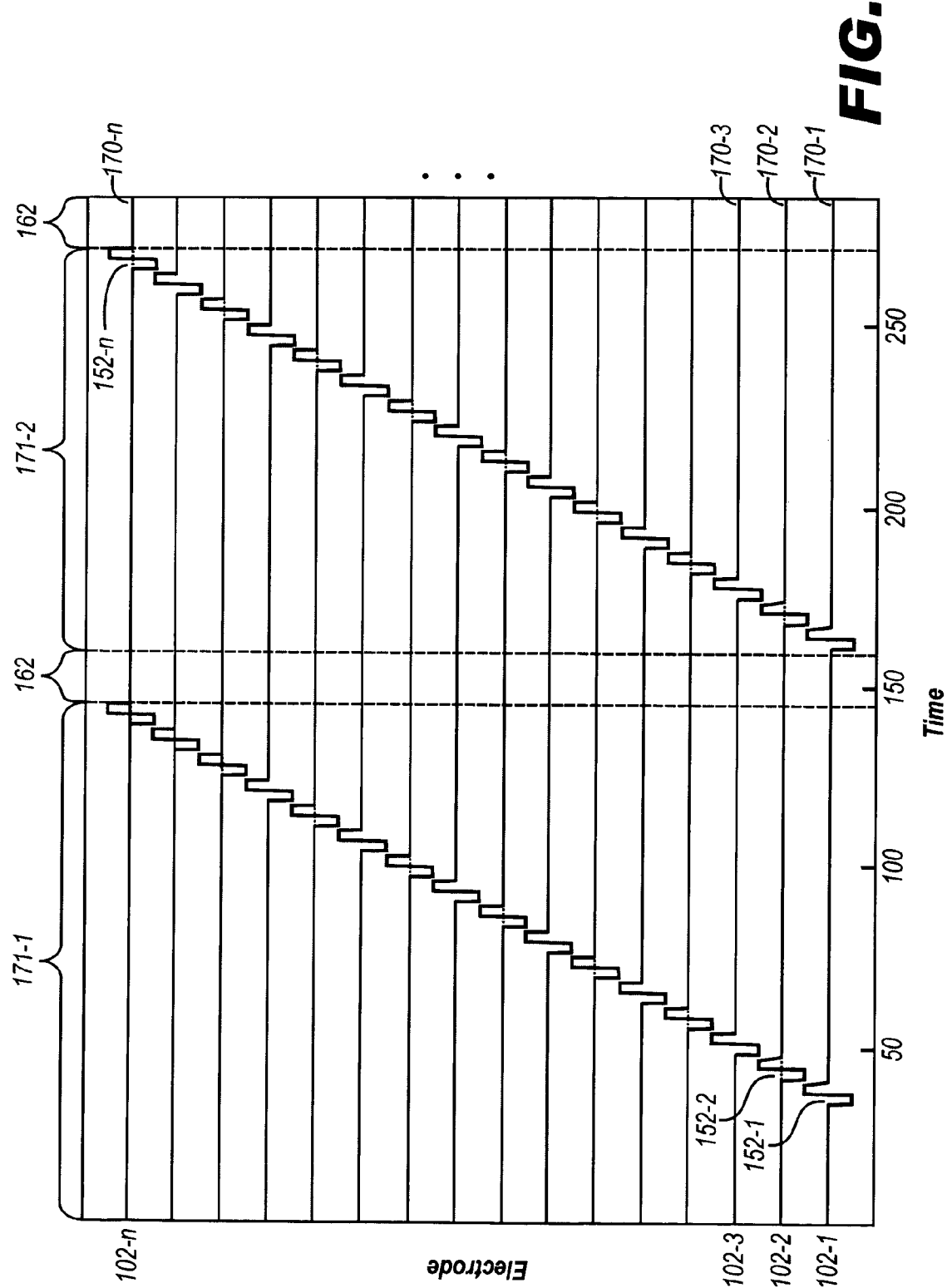
FIG. 7 illustrates another exemplary global shorting scheme wherein all of the electrodes are periodically shorted at the same time in order to remove accumulated charge therefrom according to principles described herein.

The global shorting periods (162) may be configured to follow a sequence of any number of stimulation events (152) that are applied via any number of electrodes (102). For example, FIG. 7 illustrates an exemplary global shorting scheme wherein all of the electrodes (102) are periodically shorted at the same time in order to remove accumulated charge therefrom. The diagram of FIG. 7 shows a number of exemplary stimulation pulse waveforms (170-1 through 170-n) that may be applied to one or more stimulation sites via each electrode (102-1 through 102-n) during two particular stimulation frames (171-1 and 171-2). Each waveform (170) shown in FIG. 7 includes a single stimulation event (152) during each stimulation frame (171) for illustrative purposes only. It will be recognized that each waveform (170) may include any number of stimulation events (152) as best serves a particular application.

As shown in FIG. 7, each global shorting period (162) is configured to follow a sequence of multiple stimulation events (152). The number of stimulation events (152) that occur before each global shorting period (162) may vary as best serves a particular application. For example, as shown in FIG. 7, an entire stimulation frame's worth of stimulation events (152) may occur before each global shorting period (162).

In some examples, the global shorting periods (162) occur on a periodic basis, as shown in FIGS. 6-7. However, it will be recognized that the timing of the global shorting periods (162) may alternatively be intermittent or otherwise vary as best serves a particular application.

Figure 8:
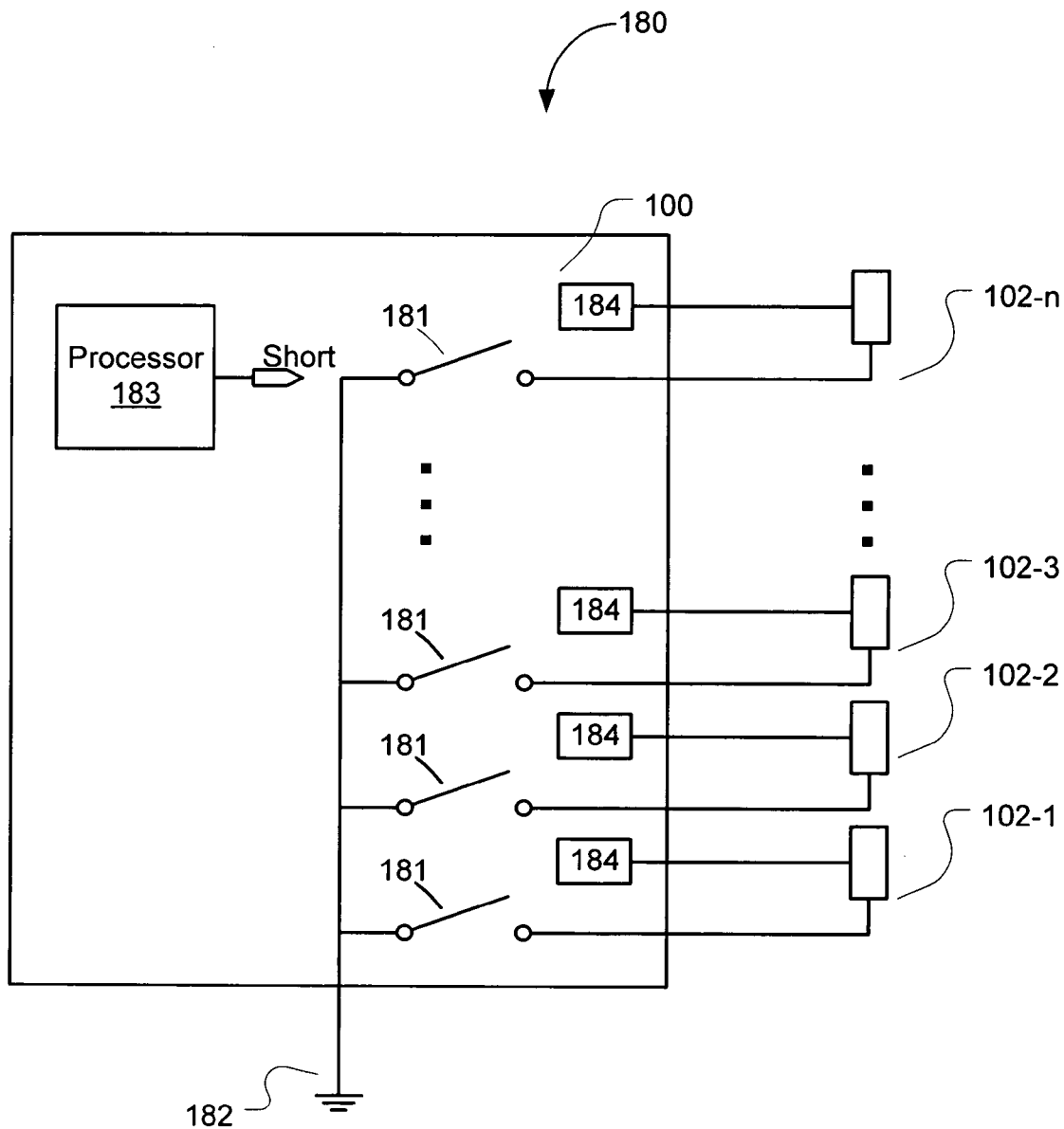
FIG. 8 illustrates an exemplary shorting system wherein one or more electrodes may be globally shorted according to principles described herein.

As mentioned, an electrode (102) may be shorted by connecting the electrode (102) to ground, a reference electrode, or any other reference voltage. FIG. 8 illustrates an exemplary shorting system (180) wherein one or more electrodes (102) may be globally shorted. FIG. 8 shows a number of exemplary components configured to simultaneously connect a number of electrodes (102) to ground. It will be recognized that the components of FIG. 8 are merely illustrative and that any combination of hardware, software, and/or firmware located within the stimulator (100), external device (101), and/or any other device may additionally or alternatively be used to short the electrodes (102).

As shown in FIG. 8, the shorting system (180) may include one or more current sources (184) coupled to each electrode (102). The current sources (184) may be located within the stimulator (100), for example, and are configured to generate one or more stimulation events that are applied to one or more stimulation sites within a patient via the electrodes (102).

The shorting system (180) may also include a number of switching elements (181) electrically coupled to ground (182). In some examples, the switching elements (181) may alternatively be electrically coupled to a reference electrode or to some other suitable reference voltage. An open node of each switching element (181) is electrically coupled to a corresponding electrode (102).

The switching elements (181) may include any number of controllable analog and/or digital devices configured to couple the electrodes (102) to ground (182). For example, the switching elements (181) may include, but are not limited to, any type or combination of transistors, diodes, logic gates, or any other combination of analog and/or digital devices.

As shown in FIG. 8, a processor (183) configured to control the switching elements (181) may be included within the shorting system (180). The processor (183) may include any combination of hardware, software, and firmware. In some examples, the processor (183) may be configured to output a digital "short" signal that causes each of the switches (181) to open or close. For example, to initiate a global shorting period, the "short" signal generated by the processor (183) may be configured to simultaneously close each of the switching elements (181). In this manner, each of the electrodes (102) is simultaneously connected to ground (182). The switching elements (181) may then be simultaneously opened at the end of the global shorting period.

It will be recognized that the electrodes (102) do not always have to be simultaneously connected to ground (182). In some alternative examples, the processor (183) may be configured to sequentially close one or more of the switching elements (181) during a pre-determined time period. The pre-determined time period may be relatively short so that the electrodes (102) are still effectively globally shorted.

In some alternative examples, only a subset of the electrodes (102) are globally shorted. The number of electrodes (102) in each subset may vary as best serves a particular application.

Figure 9:
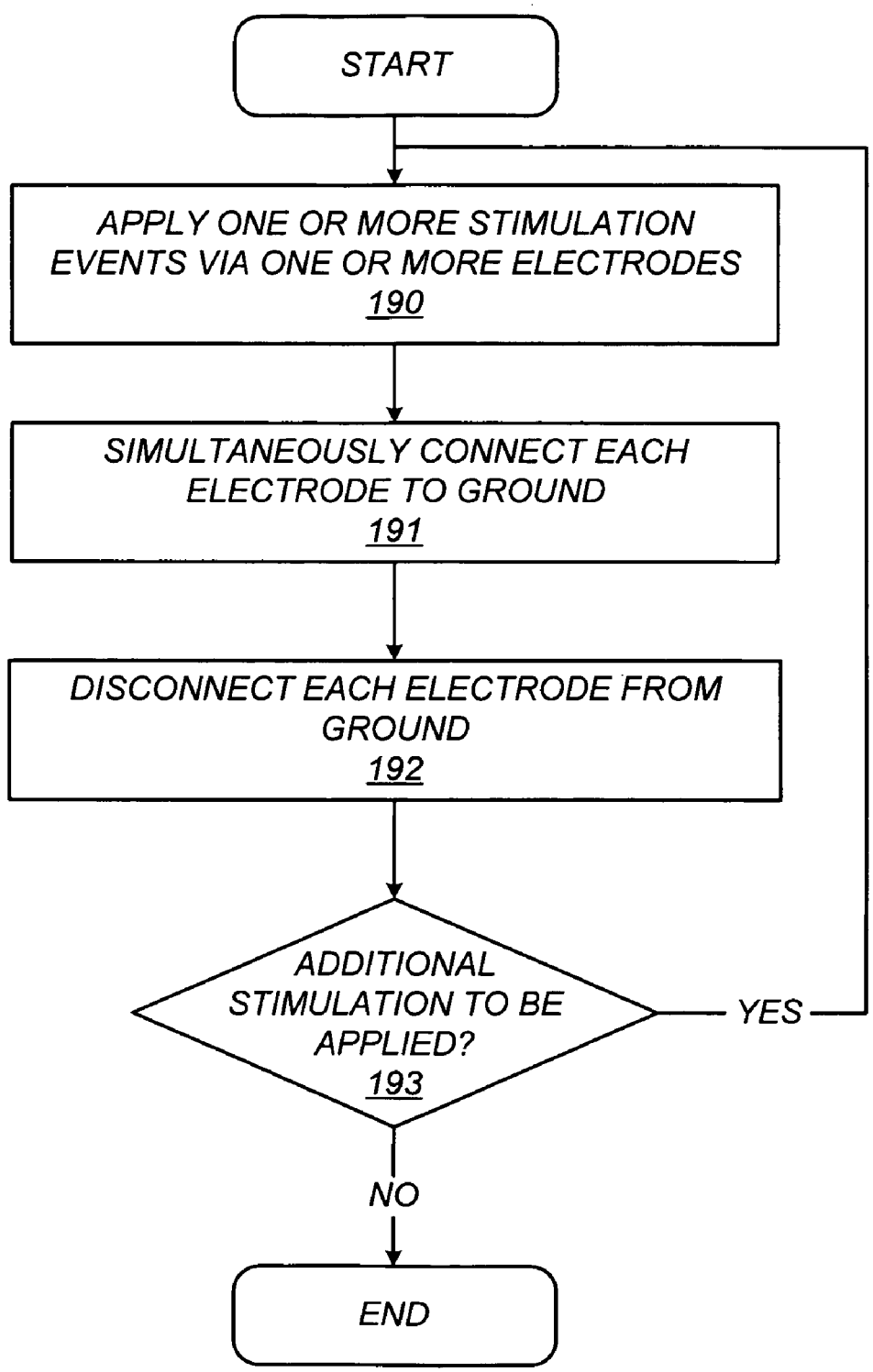
FIG. 9 is a flow chart illustrating an exemplary method of removing charge that has accumulated on one or more electrodes according to principles described herein.

FIG. 9 is a flow chart illustrating an exemplary method of removing charge that has accumulated on one or more electrodes (102). It will be recognized that the method shown in FIG. 9 is merely illustrative and that alternative methods may omit, add to, reorder, and/or modify any of the steps shown in FIG. 9.

In step 190, one or more stimulation events are applied to one or more stimulation sites within a patient. The stimulation events are applied via one or more electrodes (102) that are coupled to an implantable stimulator (100) and may include any number or type of stimulation pulses as best serves a particular application.

After a predetermined number of stimulation events have been applied to one or more stimulation sites, each electrode (102) is simultaneously connected to ground, as shown in step 191. As previously described, each electrode (102) may alternatively be connected to a reference electrode or to any other reference voltage.

The number of stimulation events that are applied to the one or more stimulation sites prior to connecting each electrode (102) to ground may vary as best serves a particular application. For example, a global shorting period may follow each stimulation event, a number of stimulation events that occur during a particular stimulation frame, or any other number of stimulation events as best serves a particular application.

By virtue of being shorted to ground, at least a portion of the excess charge that has accumulated on one or more of the electrodes (102) during one or more of the stimulation events is dissipated or removed therefrom. After a predetermined amount of time (i.e., at the end of the global shorting period), each of the electrodes (102) is disconnected from ground, as shown in step 192.

In step 193, a determination is then made as to whether additional stimulation is to be applied to the one or more stimulation sites. If additional stimulation is to be applied to the one or more stimulation sites (Yes; step 193), the process of applying one or more stimulation events and then globally shorting all of the electrodes (102) is repeated.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of removing accumulated charge from a plurality of electrodes, said method comprising:
    applying a plurality of stimulation events to one or more stimulation sites within a patient via said plurality of electrodes, each of said stimulation events comprising one or more biphasic stimulation pulses that each have first and second phases; and
    globally shorting each of said plurality of electrodes during a plurality of global shorting periods interspersed among said plurality of stimulation events;
    wherein the stimulation events are not applied to the one or more stimulation sites during each of the global shorting periods;
    wherein one of said global shorting periods immediately follows each one of said stimulation events; and
    wherein a duration of each of said global shorting periods is such that only a portion of said accumulated charge is removed from said plurality of electrodes during each of said global shorting periods and such that all of said accumulated charge is removed from said plurality of electrodes after all of said plurality of global shorting periods have occurred.

2. The method of claim 1, wherein said plurality of stimulation events are included within a stimulation frame.

3. The method of claim 1, wherein said step of globally shorting each of said plurality of electrodes during said plurality of said global shorting periods comprises connecting each of said plurality of electrodes to ground during said global shorting periods.

4. The method of claim 1, wherein said step of globally shorting each of said plurality of electrodes during said plurality of said global shorting periods comprises connecting each of said plurality of electrodes to a reference electrode during said global shorting periods.

5. The method of claim 1, wherein each of said stimulation events comprises a single biphasic stimulation pulse.

6. A system comprising:
a plurality of electrodes; and
a stimulator electrically coupled to said plurality of electrodes and configured to apply a plurality of stimulation events to one or more stimulation sites within a patient via said plurality of electrodes, each of said stimulation events comprising one or more biphasic stimulation pulses that each have first and second phases;
wherein said stimulator is further configured to globally short each of said plurality of electrodes during a plurality of global shorting periods interspersed among said plurality of stimulation events;
wherein the stimulation events are not applied to the one or more stimulation sites during each of the global shorting periods;
wherein one of said global shorting periods immediately follows each one of said stimulation events; and
wherein a duration of each of said global shorting periods is such that only a portion of said accumulated charge is removed from said plurality of electrodes during each of said global shorting periods and such that all of said accumulated charge is removed from said plurality of electrodes after all of said plurality of global shorting periods have occurred.

7. The system of claim 6, wherein said plurality of stimulation events are included within a stimulation frame.

8. The system of claim 6, wherein said stimulator is configured to globally short each of said plurality of electrodes during said plurality of said global shorting periods by connecting each of said plurality of electrodes to ground during said global shorting periods.

9. The system of claim 6, wherein said stimulator is configured to globally short each of said plurality of electrodes during said plurality of said global shorting periods by connecting each of said plurality of electrodes to a reference electrode during said global shorting periods.

10. The system of claim 6, wherein each of said stimulation events comprises a single biphasic stimulation pulse.

11. An implantable stimulator comprising:
electrical circuitry configured to apply a plurality of stimulation events to one or more stimulation sites within a patient via a plurality of electrodes, each of said stimulation events comprising one or more biphasic stimulation pulses that each have first and second phases;
one or more switching elements electrically coupled to each of said plurality of electrodes; and
a processor configured to control each of said switching elements;
wherein said processor is further configured to cause each of said switching elements to globally short each of said plurality of electrodes during a plurality of global shorting periods interspersed among said plurality of stimulation events;
wherein the electrical circuitry does not apply the stimulation events to the one or more stimulation sites during each of the global shorting periods;
wherein one of said global shorting periods immediately follows each one of said stimulation events; and
wherein a duration of each of said global shorting periods is such that only a portion of said accumulated charge is removed from said plurality of electrodes during each of said global shorting periods and such that all of said accumulated charge is removed from said plurality of electrodes after all of said plurality of global shorting periods have occurred.

12. The stimulator of claim 11, wherein said plurality of stimulation events are included within a stimulation frame.

13. The stimulator of claim 11, wherein said switching elements are configured to electrically couple each of said plurality of electrodes to ground or to a reference electrode during said global shorting periods.

14. The stimulator of claim 11, wherein said switching elements are configured to globally short each of said plurality of electrodes by simultaneously connecting each of said plurality of electrodes to ground.

15. The stimulator of claim 11, wherein said processor is configured to sequentially close one or more of said switching elements during a pre-determined time period to globally short each of said plurality of electrodes to ground.

* * * * *